(12) United States Patent
Audonnet et al.

(10) Patent No.: US 7,163,926 B1
(45) Date of Patent: Jan. 16, 2007

(54) ADJUVANT-CONTAINING VACCINES

(75) Inventors: Jean-Christophe Francis Audonnet, Lyons (FR); Jules Maarten Minke, Corbas (FR)

(73) Assignee: Merial, Lyons (FR)

(*) Notice: Subject to any disclaimer, the term of this patent is extended or adjusted under 35 U.S.C. 154(b) by 322 days.

(21) Appl. No.: 09/677,672

(22) Filed: Oct. 2, 2000

Related U.S. Application Data

(63) Continuation-in-part of application No. PCT/FR99/00666, filed on Mar. 22, 1999.

(30) Foreign Application Priority Data

Apr. 3, 1998 (FR) ................................. 98 04409

(51) Int. Cl.
*A61K 48/00* (2006.01)

(52) U.S. Cl. .................. 514/44; 424/450; 424/486; 424/468; 435/320.1

(58) Field of Classification Search ............... 514/44; 424/450, 486, 482, 468; 435/320.1
See application file for complete search history.

(56) References Cited

U.S. PATENT DOCUMENTS

| | | | | |
|---|---|---|---|---|
| 3,920,811 A | * | 11/1975 | Lund | 424/88 |
| 5,080,896 A | * | 1/1992 | Visser | 424/88 |
| 5,922,327 A | * | 7/1999 | Crabb | 424/229.1 |
| 5,989,562 A | * | 11/1999 | Wasmoen | 424/199.1 |
| 6,004,563 A | * | 12/1999 | Chu | 424/263.1 |
| 6,197,312 B1 | * | 3/2001 | Peak | 424/250.1 |
| 6,207,166 B1 | * | 3/2001 | Audonnet | 424/199.1 |
| 6,300,118 B1 | * | 10/2001 | Chavez | 435/252.3 |
| 6,312,727 B1 | * | 11/2001 | Schacht | 424/490 |
| 6,340,464 B1 | * | 1/2002 | Hilgers | 424/380.1 |
| 6,444,799 B1 | * | 9/2002 | Ross | 536/23.1 |
| 2001/0007860 A1 | * | 7/2001 | Olsen | 514/44 |
| 2001/0024653 A1 | * | 9/2001 | Gicquel | 424/200.1 |
| 2002/0164341 A1 | * | 11/2002 | Davis | 424/184.1 |

FOREIGN PATENT DOCUMENTS

| | | | | |
|---|---|---|---|---|
| EP | 0 283 085 | | * | 9/1988 |
| EP | 0 283 085 A1 | | | 9/1988 |
| EP | 0 532 833 A1 | | * | 3/1993 |
| WO | WO 95/11700 | | * | 5/1995 |
| WO | WO 96/20007 | | * | 7/1996 |
| WO | WO 98/03198 | | * | 1/1998 |

OTHER PUBLICATIONS

Cullinane, Veterinary Quaternary Review on Animal Diseases, vol. 24, No. 2, 80-94, Jun. 2002.*
Larsen, J. Virology, vol. 27, 2, 1704-1708, 1998.*

* cited by examiner

*Primary Examiner*—Dave Trong Nguyen
(74) *Attorney, Agent, or Firm*—Frommer Lawrence & Haug; Thomas J. Kowalski; Judy Jarecki Black

(57) ABSTRACT

This invention provides a DNA vaccine which comprises a naked DNA incorporating and expressing in vivo a nucleotide sequence encoding an antigenic polypeptide, preferably a gene of a pathogenic agent, and at least one adjuvant compound chosen from the polymers of acrylic or methacrylic acid and copolymers of maleic anhydride and alkenyl derivative. The adjuvant compound is preferably a carbomer or an EMA®. This invention also provides a method of enhancing a DNA vaccine and/or the immunogenicity of a DNA vaccine.

6 Claims, 6 Drawing Sheets

ATGAAGACAACCATTATTTTGATACTACTGACCCATTGGGTCTACAGTCAAAACCCAACCAGTGGCAAC
AACACAGCCACATTATGTCTGGGACACCATGCAGTAGCAAATGGAACATTGGTAAAAACAATAACTGAT
GACCAAATTGAGGTGACAAATGCTACTGAATTAGTCCAGAGCATTTCAATAGGGAAAATATGCAACAAC
TCATATAGGGTTCTAGATGGAAGAAATTGCACATTAATAGATGCAATGCTAGGAGACCCCATTGTGAT
GATTTTCAGTATGAGAATTGGGACCTCTTCATAGAAAGAAGCAGCGCTTTCAGCAATTGCTACCCATAT
GACATCCCTGACTATGCATCGCTCCGGTCCATTGTAGCATCCTCAGGAACATTAGAATTCACAGCAGAG
GGCTTCACATGGACAGGTGTCACTCAAAACGGAAGAAGTGGAGCCTGCAAAAGGGGATCAGCCGATAGT
TTCTTTAGCCGACTGAATTGGCTAACAAAATCTGGAAATTCTTACCCCATATTGAATGTGACAATGCCT
AACAATAAAAATTTCGATAAACTATACATCTGGGGATTCATCACCCGAGCTCAAACAAAGAGCAGACA
AAATTATATATCCAAGAATCAGGACGAGTAACAGTCTCAACAGAAAGAAGTCAACAAACAGTAATCCCT
AACATCGGATCTAGGCCGTGGGTCAGGGTCAATCAGGCAGGATAAGCATATACTGGACCATTGTAAAA
CCTGGAGATATTCTAATGATAAACAGTAATGGCAACTTAGTTGCACCGCGGGATATTTTAAATTGAGA
ACAGGGAAAAGCTCTGTAATGAGATCAGATGCACTCATAGACACTTGTGTGTCTGAATGTATTACACCA
AATGGAAGCATCCCCAACGACAAACCATTTCAAAATGTGAACAAAATTACATATGGAAAATGCCCCAAG
TATATCAGGCAAAACACTTTAAAGCTGGCCACTGGGATGAGGAATGTACCAGAAAAGCAAATCAGAGGA
ATCTTTGGAGCAATAGCGGGATTCATAGAAAACGGCTGGAAGGAATGGTTGATGGGTGGTATGGATTC
CGATATCAAAACTCGGAAGGAACAGGACAAGCTGCAGATCTAAAGAGCACTCAAGCAGCCATAGACCAG
ATCAATGGAAAATTAAACAGAGTGATTGAAAGGACCAATGAGAAATTCCATCAAATAGAAAAGGAATTC
TCAGAAGTAGAAGGGAGAATCCAGGATTTGGAGAAGTATGTAGAAGACACCAAAATAGACCTATGGTCC
TACAATGCAGAATTGCTGGTGGCTCTAGAAAATCAACATACAATTGACTTAACAGATGCAGAAATGAAT
AAATTATTCGAAGACTAGGCGCCAGTTAAGAGAAAACGCGGAAGACATGGAGGTGGATGTTTCAAG
ATTTACCACAAATGTGATAATGCATGCATTGGATCAATAAGAAATGGGACATATGACCATTACATATAC
AGAGATGAAGCATTAAACAACCGATTTCAAATCAAAAGTGTTGAGTTGAAATCAGGCTACAAAGATTGG
ATACTGTGGATTTCATTCGCCATATCATGCTTCTTAATTTGCGTTGTTCTATTGGGTTTCATTATGTGG
GCTTGCCAAAAAGGCAACATCAGGTGCAACATTTGCATTTGA

SEQ ID NO:3

FIGURE 1

```
ATGAAGACAACCATTATTTTGATACTACTGACCCATTGGGTCTACAGTCAAAACCCAACCAGTGGCAA
CAACACAGCCACATTATGTCTGGGACACCATCCAGTAGCAAATGGAACATTGGTAAAAACAATAACTG
ATGACCAAATTGAGGTGACAAATGCTACTGAATTAGTTCAGAGCATTTCAATAGGGAAAATATGCAAC
AACTCATATAGAGTTCTAGATGGAAGAAATTGCACATTAATAGATGCAATGCTAGGAGACCCCCACTG
TGATGTCTTTCAGTATGAGAATTGGGACCTCTTCATAGAAAGAAGCAGCGCTTTCAGCAATTGCTACC
CATATGACATCCCTGACTATGCATCGCTCCGGTCCATTGTAGCATCCTCAGGAACATTGGAATTCACA
GCAGAGGGATTCACATGGACAGGTGTCACTCAAAACGGAAGAAGTGGAGCCTGCAAAAGGGGATCAGC
CGATAGTTTCTTTAGCCGACTGAATTGGCTAACAAAATCTGGAAACTCTTACCCCACATTGAATGTGA
CAATGCCTAACAATAAAAATTTCGACAAACTATACATCTGGGGATTCATCACCCGAGCTCAAACCAA
CAGCAAACAGAATTGTACATCCAAGAATCAGGACGAGTAACAGTCTCAACAAAAGAAGTCAACAAAC
GATAATCCCTAATATCGGATCTAGACCGTGGGTCAGGGGTCAATCAGGCAGGATAAGCATATACTGGA
CCATTGTAAAACCTGGAGATATCCTAATGATAAACAGTAATGGCAACTTAGTTGCACCGCGGGATAT
TTTAAATTGAAAACAGGGAAAAGCTCTGTAATGAGATCAGATGCACCCATAGACATTTGTGTGTCTGA
ATGTATTACACCAAATGGAAGCATCCCCAACGACAAACCATTTCAAAATGTGAACAAAGTTACATATG
GAAAATGCCCCAAGTATATCAGGCAAAACACTTTAAAGCTGGCCACTGGGATGAGGAATGTACCAGAA
AAGCAAATCAGAGGAATCTTTGGAGCAATAGCGGGATTCATAGAAAACGGCTGGAAGGAATGGTTGA
TGGGTGGTATGGATTCCGATATCAAAACTCGGAAGGAACAGGACAAGCTGCAGATCTAAAGAGCACTC
AAGCAGCCATCGACCAGATTAATGGAAAATTAAACAGAGTGATTGAAAGGACCAATGAGAAATTCCAT
CAAATAGAGAAGGAATTCTCAGAAGTAGAAGGGAGAATCCAGGACTTGGAGAAGTATGTAGAAGACAC
CAAAATAGACCTATGGTCCTACAATGCAGAATTGCTGGTGGCTCTAGAAAATCAACATACAATTGACT
TAACAGATGCAGAAATGAATAAATTATTCGAGAAGACTAGACGCCAGTTAAGAGAAAACGCGGAAGAC
ATGGGAGGTGGATGTTTCAAGATTTACCACAAATGTGATAATGCATGCATTGGATCAATAAGAAATGG
GACATATGACCATTACATATACAGAGATGAAGCATTAAACAACCGATTTCAAATCAAGGTGTTGAGT
TGAAATCAGGCTACAAAGATTGGATACTGTGGATTTCATTCGCCATATCATGCTTCTTAATTTGCGTT
GTTCTATTGGGTTTCATTATGTGGGCTTGCCAAAAAGGCAACATCAGATGCAACATTTGCATTTGA
```

SEQ ID NO:5

FIGURE 2

```
ATGAACCCAAATCAAAAGATAATAACAATTGGATCTGCATCATTAGGAGTACTAATCCTCAACGTCATT
CTCCATGTAGTCAGCATTATAGTAACAGTACTGGTTCTCAATAACAATGGAACAGGTCTGAACTGCAAC
GGGACGATCATAAGAGAGTACAATGAAACAGTAAGAGTAGAAAGAATCACCCAATGGTATAATACTAGT
ACAATTGAGTACATAGAAAGATCTTCAAATGAATACTACATGAACAACACCGAACCACTTTGTGAGGCC
CAGGGCTTTGCACCATTTTCCAAAGACAATGGAATACGAATTGGGTCGAGAGGCCATGTTTTTGTAATA
AGAGAACCTTTTGTATCATGTTCGCCCTCAGAATGTAGAACCTTTTTCCTCACACAGGGCTCATTACTC
AATGACAAACATTCTAACGGCACAGTGAAGGACCGAAGTCCATATAGGACTTTGATGAGTGTCAAAATA
GGGCAATCACCTAATGTGTATCAAGCTAGGTTTGAATCGGTGGCATGGTCAGCAACAGCATGCCATGAT
GGAAAAAAATGGATGACAGTTGGAGTCACAGGGCCCGACAATCAAGCAGTTGCAGTAGTGAACTATGGA
GGTGTTCCGGTTGATATTATTAATTCATGGGCATGGATATCTTAAGAACCCAAGAATCGTCATGCACC
TGCATTAAAGGAGACTGTTATTGGGTGATGACTGATGGACCGGCAAACAGGCAAGCTAAATATAGGATA
TTCAAAGCAAAAAATGGAAGAATAATTGGGCAGACTGATATAAGTTTCAATGGGGACACATAGAGGAG
TGTTCTTGTTACCCCAATGAAGGGAAGGTGGAATGCATATGCAGGGACAACTGGACTGGAACAAATAGA
CCAATTCTGGTAATATCTTCTGATCTATCGTACACAGTCGGATATTTGTGTGCTGGCATTCCCACTGAC
ACTCCTAGGGGAGAGGATAGTCAATTCACAGGCTCATGTACAAGCCCTTTGGGAAATAAAGGATACGGT
GTAAAAGGTTTCGGGTTTCGACAAGGAACTGACGTATGGGCCGGAAGGACAATTAGTAGGACTTCAAGA
TCAGGATTCGAAATAATAAAGATCAGGAATGGTTGGACACAGAATAGTAAAGATCAAATCAGAAGGCAA
GTGATTATTGATAACCTAAATTGGTCAGGATATAGCGGTTCTTTCACATTGCCGGTTGAACTAACAAAA
AAGGGATGTTTAGTCCCCTGTTTCTGGGTTGAAATGATTAGAGGTAAACCTGAAGAAACAACAATATGG
ACCTCTAGCAGCTCCATTGTGATGTGTGGAGTAGATCATAAAGTTGCCAGTTGGTCATGGCACGATGGA
GCTATTCTTCCCTTTGACATCGATAAGATGTAA
```

SEQ ID NO:8

FIGURE 3

ATGAATCCAAATCAAAAGATAATAACAATTGGATCTGCATCATTGGGAATATTAATCATCAACGTCATT
CTCCATGTAGTCAGCATTATAGTAACAGTACTGGTCCTCAATAACAATGGAACAGGTCTGAACTGCAAA
GGGACGATCATAAGAGAGTACAATGAAACAATAAGAGTAGAAAGAATTACTCAATGGTATAATACCAGT
ACAATTGAGTACATAGAGAGACCTTCAAATGAATACTACATGAACAACACCGAACCACTTTGTGAGGCC
CAAGGCTTTGCACCATTTTCCAAAGATAATGGAATACGAATTGGGTCGAGAGGCCATGTTTTTGTAATA
AGAGAACCTTTTGTCTCATGTTCCCCCTCAGAATGTAGAACCTTTTTCCTCACACAGGGCTCATTACTC
AATGACAAACATTCTAACGGCACAGTGAAGGACCGAAGTCCATATAGGACTTTGATGAGTGTCAAAATA
GGGCAATCACCTAATGTGTATCAAGCTAGGTTTGAATCGGTGGCATGGTCAGCAACAGCATGCCATGAT
GGAAAAAAATGGATGACAGTTGGAGTCACAGGGCCCGATAATCAAGCAATTGCAGTAGTGAACTATGGA
GGTGTTCCGGTTGATATTATTAATTCATGGGCAGGGGATATCTTAAGAACCCAAGAATCGTCATGCACC
TGCATTAAAGGAGACTGTTATTGGGTGATGACTGATGGACCGGCAAATAGGCAAGCTAAATATAGGATA
TTCAAAGCAAAAGATGGAAGAATAATTGGGCAGACTGATATAAGTTTCAATGGGGACACATAGAGGAG
TGTTCTTGTTACCCCAATGAAGGGAAGGTGGAATGCATATGCAGGGACAACTGGACTGGAACAAATAGA
CCAATTCTGGTAATATCTTCTGATCTATCGTACACAGTCGGATATTTGTGTGCTGGCATTCCCACTGAC
ACTCCTAGGGGAGAGGATAGTCAATTCACAGGCTCATGTACAAGTCCTTTGGAAATAAAGGATACGGT
GTAAAAGGTTTCGGGTTTCGACAAGGAACTGACGTATGGGCCGGAAGGACAATTAGTAGGACTTCAAGA
TCAGGATTCGAAATAATAAAAATCAGGAATGGTTGGACACAGAACAGTAAAGACCAAATCAGAAGGCAA
GTGATTATTGATAACCCAAATTGGTCAGGATATAGCGGTTCTTTCACATTGCCGGTTGAACTAACAAAA
AAGGGATGTTTAGTCCCTGTTTCTGGGTTGAAATGATTAGAGGTAAACCTGAAGAAACAACAATATGG
ACCTCTAGCAGCTCCATTGTCATGTGTGGAGTAGATCATAAAATTGCCAGTTGGTCATGGCACGATGGA
GCTATTCTTCCCTTTGACATAGACAAGATGTAG

SEQ ID NO:9

FIGURE 4

ATGGCGTCTCAAGGCACCAAACGATCTTATGAGCAGATGGAAACTGATGGGGAACGCCAGAATGC
AACTGAAATCAGAGCATCTGTCGGAAGGATGGTGGGAGGAATCGGCCGGTTTTATGTTCAGATGT
GTACTGAGCTTAAATTAAACGACCATGAAGGCGGCTGATTCAGAACAGCATAACAATAGAAAGG
ATGGTACTTTCGGCATTCGACGAAAGAAGAAACAAGTACCTCGAGGAGCATCCCAGTGCTGGGAA
AGACCCTAAGAAAACGGGAGGCCCGATATACAGAAGGAAAGATGGGAAATGGATAAGAGAACTCA
TCCTCCATGATAAAGAGGAAATCATGAGGGTCTGGCGTCAGGCCAACAATGGTGAAGATGCTACT
GCTGGTCTTACCCATATGATGATCTGGCACTCCAATCTCAATGACACCACATACCAAAGAACAAG
GGCTCTTGTTCGGACTGGGATGGATCCCAGAATGTGCTCTCTGATGCAAGGATCAACCCTCCCAC
GGAGATCTGGAGCTGCCGGTGCTGCAGTAAAAGGTGTTGGAACAATGATAATGGAACTCATCAGG
ATGATCAAACGCGGATAAATGATCGAAATTTCTGGAGAGGTGAAAATGGTCGAAGAACCAGAAT
TGCTTATGAAAGAATGTGCAATATCCTCAAAGGGAAATTTCAAACAGCAGCACAACGGGCTATGA
TGGACCAAGTGAGGGAGGGCCGCAATCCTGGAAATGCTGAGATTGAGGATCTCATTTTCTTGGCA
CGATCAGCACTCATTTTGAGAGGATCAGTAGCCCATAAATCATGCCTACCTGCCTGTGTTTATGG
CCTTGCAGTAACCAGTGGGTATGACTTTGAGAAGGAAGGATACTCTCTGGTTGGGATTGATCCTT
TCAAACTACTCCAGAACAGCCAAATTTTCAGTCTAATCAGACCGAAAGAAAATCCAGCACACAAG
AGCCAGTTGGTGTGGATGGCATGCCATTCTGCAGCATTTGAGGACCTGAGAGTTTTGAATTTCAT
TAGAGGAACAAAAGTAATCCCAAGAGGACAGTTGGCAACCAGAGGAGTGCAGATTGCTTCAAATG
AAAACATGGAGACAATAGATTCTAGCACACTCGAACTGAGAAGCAGATATTGGGCAATAAGGACC
AGAAGTGGAGGAAACACCAGTCAACAGAGAGCATCTGCAGGACAGATAAGTGTGCAACCTACTTT
CTCAGTGCAGAGAAATCTTCCCTTTGAAAGAGCAACCATTATGGCTGCATTTACTGGGAACACTG
AGCGGAGGACTTCCGACATGAGAACGGAAATCATAAGGATGATGGAAAATGCCAAATCAGAAGAT
GTGTCTTTCCAGGGCGGGGAGTCTTCGAGCTCTCGGACGAAAAGGCAACGAACCCGATCGTGCC
TTCCTTTGACATGAGCAATGAAGGGTCTTATTTCTTCGGAGACAATGCTGAGGAGTATGACAGTT
AA

SEQ ID NO:12

FIGURE 5

ATGGCGTCTCAAGGCACCAAACGATCTTATGAGCAGATGGAAACTGATGGGGAACGCCAGAATGCAACT
GAAATCAGAGCATCTGTCGGAAGGATGGTGGGAGGAATCGGCCGGTTTTATGTTCAGATGTGTACTGAG
CTTAAACTAAACGACCATGAAGGGCGGCTGATTCAGAACAGCATAACAATAGAAAGGATGGTACTCTCG
GCATTCGACGAAAGAAGAAACAAGTATCTCGAGGAGCATCCCAGTGCTGGGAAGACCCTAAGAAACG
GGAGGCCCGATATACAGAAGGAAAGATGGGAAATGGATGAGAGAACTCATCCTCCATGATAAAGAAGAA
ATCATGAGGATCTGGCGTCAGGCCAACAATGGTGAAGACGCTACTGCTGGTCTTACTCATATGATGATC
TGGCACTCCAATCTCAATGACACCACATACCAAAGAACAAGGGCTCTTGTTCGGACTGGGATGGATCCC
AGAATGTGCTCTCTGATGCAAGGCTCAACCCTCCCACGGAGATCTGGAGCCGCTGGTGCTGCAGTAAAA
GGTGTTGGAACAATGGTAATGGAACTCATCAGAATGATCAAACGCGGATAAATGATCGGAATTTCTGG
AGAGGTGAAAATGGTCGAAGAACCAGAATTGCTTATGAAAGAATGTGCAATATCCTCAAAGGGAAATTT
CAGACAGCAGCACAACGGGCTATGATGGACCAGGTGAGGGAAGGCCGCAATCCTGGAAACGCTGAGATT
GAGGATCTCATTTTCTTGGCACGATCAGCACTTATTTTGAGAGGATCAGTAGCCCATAAATCATGCCTA
CCTGCCTGTGTTTATGGCCTTGCAGTAACCAGTGGGTATGACTTTGAGAAGGAAGGATACTCTCTGGTT
GGAATTGATCCTTTCAAACTACTCCAGAACAGCCAAATTTTCAGTCTAATCAGACCGAAAGAAACCCA
GCACACAAGAGCCAGTTGGTGTGGATGGCATGCCATTCTGCAGCATTTGAGGACCTGAGAGTTTTGAAT
TTCATTAGAGGAACCAAAGTAATCCCAAGAGGACAGTTAGCAACCAGAGGAGTGCAAATTGCTTCAAAT
GAAAACATGGAGACAATAGATTCTAGCACACTCGAACTGAGAAGCAAATATTGGGCAATAAGGACCAGA
AGTGGAGGAAACACCAGTCAACAGAGAGCATCTGCAGGACAGATAAGTGTGCAACCTACTTTCTCAGTG
CAGAGAAATCTTCCCTTTGAAAGAGCAACCATTATGGCTGCATTCACTGGGAACACTGAAGGGAGGACT
TCCGACATGAGAACGGAAATCATAAGGATGATGGAAAATGCCAAATCAGAAGATGTGTCTTTCCAGGGG
CGGGGAGTCTTCGAGCTCTCGGACGAAAAGGCAACGAACCCGATCGTGCCTTCCTTTGACATGAGCAAT
GAAGGGTCTTATTTCTTCGGAGACAATGCTGAGGAGTTTGACAATTAA

SEQ ID NO:13

FIGURE 6

ADJUVANT-CONTAINING VACCINES

CROSS-REFERENCE TO RELATED APPLICATIONS/INCORPORATION BY REFERENCE

This application is a continuation-in-part of PCT/FR99/00666, filed on Mar. 22, 1999 which claims the priority benefits of French Patent Application No. 98/04409, filed on Apr. 3, 1998. Each of these applications, as well as each document or reference cited in each of these applications (including during the prosecution; "application cited documents"), and each foreign application or patent corresponding to and/or claiming priority from any of these applications, and each of the documents cited or referenced in each of the application cited documents, are hereby expressly incorporated herein by reference in their entirety. More generally, documents or references are cited in this text; and, each of these documents or references ("herein-cited documents or references"), as well as each document or reference cited in each of the herein-cited documents or references (including any manufacturer's specifications, instructions, etc.), is hereby expressly incorporated herein by reference.

FIELD OF THE INVENTION

The present invention relates to an improvement to DNA vaccines, also called plasmid or polynucleotide vaccines, comprising and expressing in vivo one or more heterologous genes. It relates in particular to such improved vaccines, to the use of particular adjuvant compounds for using such vaccines as well as to the vaccination methods relating thereto. Its subject is also a method of preparing these vaccines.

BACKGROUND OF THE INVENTIONS

Patent applications WO-A-90 11092, WO-A-93 19183, WO-A-94 21797, WO-A-95 11307 and WO-A-95 20660 have made use of the recently developed technique of polynucleotide vaccines. It is known that these vaccines use a plasmid capable of expressing, in the cells of the host, a gene inserted into the plasmid and encoding an immunogen. All routes of administration have been proposed (intraperitoneal, intravenous, intramuscular, transcutaneous, intradermal, mucosal, and the like). Various means of vaccination may also be used, such as DNA deposited at the surface of gold particles and discharged so as to penetrate into the cells of the skin of the animal (Tang et al., Nature 356, 152–154, 1992) and liquid jet injectors make it possible to transfect into the skin, muscle, fatty tissues and mammary tissues (Furth et al., Analytical Biochemistry, 205, 365–368, 1992).

These polynucleotide vaccines may be used in the form of naked DNA or in the form of a complex with liposomes or cationic lipids.

SUMMARY OF THE INVENTION

The objective of the invention is to enhance the efficacy of DNA vaccines by providing new vaccine formulations which are simple and easy to prepare.

Its objective is also to provide such a solution which does not cause strong interactions between the DNA and the other ingredient, which are capable of leading to the formation of a complex.

Its objective is also to provide such a solution which makes it possible, either by simple mixing, to prepare stable vaccines, formulated in a liquid form, or to easily prepare a liquid vaccine by mixing immediately before use.

The applicant has found, surprisingly, that the carbomer class of compounds meet these various objectives and in particular are capable of acting as adjuvants for naked DNA vaccines in a simple manner but in very advantageous proportions.

DETAILED DESCRIPTION

The subject of the of the present invention is therefore a DNA vaccine comprising a naked DNA, in particular circular vaccinal plasmid, supercoiled or otherwise, or a linear DNA molecule, incorporating and expressing in vivo a nucleotide sequence encoding an antigenic polypeptide, preferably a gene of a pathogenic agent, and at least one adjuvant compound chosen from the polymers of acrylic or methacrylic acid and the copolymers of maleic anhydride and alkenyl derivative.

Naked DNA is understood to mean, as in nowadays commonly accepted, a DNA transcription unit in the form of a polynucleotide sequence comprising at least one nucleotide sequence encoding an antigentic polypeptide or an antigen of one valency and the elements necessary for its expression in vivo. These elements can include a promoter, origin of replication, and transcription termination sequence. The circular plasmid form, supercoiled or otherwise, is preferred. Valency in the present invention is understood to mean at least one antigen providing protection against a pathogen, it being possible for the valency to contain, as subvalency, one or more natural or modified genes, or one or more strains of the pathogen considered.

The preferred adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 (incorporated herein by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are cross-linked with an allyl sucrose or with allyl pentaerythritol. Among them, there may be mentioned Carbopol® 974P, 934P and 971P.

Among the copolymers of maleic anhydride and alkenyl derivative, the copolymers EMA® (Monsanto)=which are copolymers of maleic anhydride and ethylene, linear or cross-linked, for example cross-linked with divinyl ether, are preferred. Reference may be made to J. Fields et al., Nature, 186: 778–780, 4 Jun. 1960, incorporated herein by reference.

From the point of view of their structure, the polymers of acrylic or methacrylic acid and the copolymers EMA® are preferably formed of basic units of the following formula:

$$-\underset{\underset{COOH}{|}}{\overset{\overset{R_1}{|}}{C}}-(CH_2)_x-\underset{\underset{COOH}{|}}{\overset{\overset{R_2}{|}}{C}}-(CH_2)_y-$$

in which:

$R_1$ and $R_2$, which are identical or different, represent H or $CH_3$ x=0 or 1, preferably x=1 y=1 or 2, with x+y=2

For the copolymers EMA®, x=0 and y=2. For the carbomers, x=y=1.

The dissolution of these polymers in water leads to an acid solution which will be neutralized, preferably to physiological pH, in order to give the adjuvant solution into which the vaccine itself will be incorporated. The carboxyl groups of the polymer are then partly in COO⁻ form.

Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCl 9 g/l) all at once or in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form.

The polymer concentration in the final vaccine composition will be 0.01% to 2% w/v, more particularly 0.06 to 1% w/v, preferably 0.1 to 0.6% w/v.

For the vaccination of pigs, the invention may apply in particular to vaccination against Aujeszky's disease virus (PRV or pseudorabies virus), porcine influenza virus (SIV), porcine reproductive and respiratory syndrome virus (PRRS virus), porcine parvovirosis virus (PPV virus), hog cholera virus (HCV virus) and bacterium responsible for actinobacillosis (*A. pleuropneumoniae*). The plasmids which can be used in the invention comprise, for each valency, one or more of the genes encoding major immunogens of the pathogenic agents considered. There may be mentioned in particular the gB and gD genes for the Aujeszky's disease virus, the HA, NP and N genes for the porcine influenza virus, the ORF5 (E), ORF3 and ORF6 (M) genes for the PRRS virus, VP2 for the parvovirosis virus, E2, E1+E2, E1+E2+C for the hog cholera virus and apxI, apxII and apxIII for *A. pleuropneumoniae*. In a particularly advantageous manner, reference may be made to the polynucleotide vaccine formulas described in patent application WO-A-98 03 658 (FR-A-2,751,224) which is incorporated herein by reference and relates to vaccines against pig reproductive and respiratory pathologies. This application describes in particular a number of plasmids which may be directly used by way of examples in the context of the present invention in combination with an adjuvant according to the invention. Persons skilled in the art will thus be able to combine, with the adjuvants in accordance with the invention, the plasmids specifically described in this previous application, namely pAB090 comprising the gB gene of the PRV virus, pPB098 comprising the gD gene of the PRV virus, pPB143 comprising the HA gene of porcine influenza, strain H1N1, pPB142 comprising the NP gene of porcine influenza, strain H1N1, pPB144 comprising the HA gene of porcine influenza, strain H3N2, pPB132 comprising the NP gene of porcine influenza, strain H3N2, pAB025 comprising ORF5 of the PRRS virus, strain Lelystad, pAB001 comprising ORF5 of the PRRS virus, strain USA, pAB091 comprising ORF3 of the PRRS virus, strain Lelystad, pAB092 comprising ORF3 of the PRRS virus, strain USA, pAB004 comprising the VP2 gene of the porcine parvovirus, pAB069 comprising the E1 gene of the hog cholera virus (HCV), pAB061 comprising the E2 gene of the hog cholera virus (HCV), pAB162 comprising the deleted apxI gene of *A. pleuropneumoniae*, pPB163 comprising the deleted apxII gene of *A. pleuropneumoniae*, pPB174', pPB189 and pPB190 comprising the deleted apxIII gene of *A. pleuropneumoniae*.

For the vaccination of horses, there may be mentioned in particular vaccination against equine rhinopneumonia virus (EHV), especially type 1 (EHV-1) and type 4 (EHV-4), against the equine influenza virus EIV, against tetanus (*Cl. tetani*), against the Eastern encephalitis virus (EEV), Western encephalitis virus (WEV) and Venezuelan encephalitis virus (VEV), as well as against Lyme disease (*B. burgdorferi*), against equine arthritis (EAV) and against rabies. Among the genes encoding major immunogens which can be used according to the invention, there may be mentioned gB and gD genes for the equine rhinopneumonia valency, especially types 1 and 4, the HA, NA and NP genes for equine influenza, the C subunit, optionally modified by mutation or deletion, for the tetanus valency, the C and E2 genes for encephalites, the OspA, OspB and p100 genes for Lyme disease, the E, M and N genes for equine arthritis and the G gene for rabies. Such polynucleotide vaccine formulas against horse pathologies are described in particular in patent application WO-A-98 03 198 (FR-A-2,751,226) which is incorporated herein by reference. This application describes a number of plasmids which can be directly used in the present invention in combination with an adjuvant in accordance with the invention. Persons skilled in the art will therefore be able to combine, with the adjuvant in accordance with the invention, a plasmid as precisely described in this application, namely pAB042 comprising the gB gene of the EHV-1 virus, pAB031 comprising the gB gene of the EHV-4 virus, pAB013 comprising the gD gene of the EHV-1 virus, pAB032 comprising the gD gene of the EHV-4 virus, pAB043 comprising the HA gene of equine influenza, Prague strain, pAB033 comprising the HA gene of equine influenza, Suffolk strain, pAB099 comprising the HA gene of equine influenza, Fontainebleau strain, pAB085 comprising the NP gene of equine influenza, Prague strain, pAB084 comprising the NP gene of equine influenza, Jillin strain, pAB070 comprising the gene for the C subunit of the tetanus toxin, pAB017 comprising the OspA gene of *Borrelia burgdorferi*, pAB094 comprising the E2 gene of the Eastern encephalitis virus, pAB093 comprising the C gene of the Eastern encephalitis virus, pAB096 comprising the E2 gene of the Western encephalitis virus, pAB095 comprising the C gene of the Western encephalitis virus, pAB098 comprising the E2 gene of the Venezuelan encephalitis virus, pAB097 comprising the C gene of the Venezuelan encephalitis virus and pAB041 comprising the G gene of the rabies virus.

For vaccination of dogs, the invention may apply in particular to vaccination against Canine Distemper (Carré's disease) virus (CDV), canine parvovirus (CPV), canine coronavirus (CCV), canine herpesvirus (CHV), Lyme disease and rabies. Among the genes encoding major immunogens which can be used in the context of the present invention, there may be mentioned most particularly the HA, F, M and N genes for the Canine Distemper virus, the VP2 gene for the canine parvovirus, the S and M genes for the canine coronavirus (CCV), the gB and gD genes for the CHV virus, the OspA and OspB and p100 genes for *B. burgdorferi* (Lyme disease) and the G gene for rabies. Such polynucleotide vaccine formulas are described in particular in patent application WO-A-98 03 199 (FR-A-2,751,227) which is incorporated herein by reference. Persons skilled in the art will therefore be able to refer to the plasmids described in this application, in combination with the adjuvants in accordance with the invention. Most particularly, they will be able to combine, with the adjuvants in accordance with the invention, the specific plasmids described in this application, namely pAB044 comprising the HA gene of CDV, pAB036 comprising the F gene of CDV, pAB024 comprising the VP2 gene of the canine parvovirus, pAB021 comprising the S gene of CCV, pAB022 comprising the M gene of CCV, pAB037 comprising the gB gene of CHV, pAB038 comprising the gD gene of CHV, pAB017 comprising the OspA gene of *B. burgdorferi* and pAB041 comprising the G gene of the rabies virus.

For vaccination of bovines, the invention may apply in particular to vaccination against the bovine herpesvirus type 1 or 5 (BHV-1 and BHV-5, responsible for the nervous form of the disease), the bovine respiratory syncytial virus (BRSV), the mucosal disease virus or bovine pestivirus (BVD), the bovine parainfluenza virus type 3 (BPI-3). Among the genes encoding the major immunogens allowing vaccination against these viruses, there may be mentioned in particular the gB and gD genes for the bovine herpesvirus, F and G for the bovine respiratory syncytial virus, E2, C+E1+E2 and E1+E2 for the mucosal disease virus, HN and F for the bovine parainfluenza virus type 3. Such vaccine formulas are described in particular in patent application WO-A-98 03 200 (FR-A-2,751,229) which is incorporated herein by reference. Persons skilled in the art will therefore be able to use the plasmids described in this application in combination with the adjuvants in accordance with the invention. In particular, they will be able to combine, with the adjuvants in accordance with the invention, the plasmids specifically described in this application, namely pPB156 comprising the gB gene of BHV-1, pAB087 comprising the gD gene of BHV-1, pAB011 comprising the F gene of BRSV, pAB012 comprising the G gene of BRSV, pAB058 comprising the C gene of BVD, pAB059 comprising the E1 gene of BVD, pAB060 comprising the E2 gene of BVD, pAB071 comprising the HN gene of BPI-3, pAB072 comprising the F gene of BPI-3.

For the vaccination of cats, the invention may apply in particular to vaccination against the feline leukemia virus FeLV, in particular subtypes A and B, the feline panleukopenia virus (FPV), the feline infectious peritonitis virus (FIPV), the coryza virus or feline herpesvirus (FHV), the feline calicivirosis virus (FCV), the feline immunodeficiency virus (FIV) and the rabies virus (rhabdovirus). Among the genes encoding major immunogens allowing vaccination against these pathogens, there may be mentioned in particular the env and gag/pol genes for feline leukemia, VP2 for panleukopaenia, M and modified S (FR-A-2,724,385 incorporated herein by reference) for infectious peritonitis, gB and gD for coryza, capsid for calicivirosis, env and gag/pro for feline immunodeficiency and G for rabies. Polynucleotide vaccine formulas are thus described in patent application WO-A-98 03 660 (FR-A-2, 751,223) which is incorporated herein by reference. Persons skilled in the art will be able to combine plasmids as described in this application with the adjuvants in accordance with the invention. In particular, they will be able to combine, with the adjuvants in accordance with the invention, the plasmids specifically described in this application, namely pPB179 comprising the env gene of the FeLV-A virus, pPB180 comprising the env gene of the FeLV-B virus, pPB181 comprising the gag/pol gene of FeLV-A, pAB009 comprising the VP2 gene of FPV, pAB053 comprising the modified S gene (FR-A-2 724 385) of the FIPV virus, pAB052 comprising the M gene of FIPV, pAB056 comprising the N gene of FIPV, pAB028 comprising the gB gene of FHV, pAB029 comprising the gD gene of FHV, pAB010 comprising the C gene of FCV, pAB030 comprising the env gene of FIV, pAB083 comprising the gag/pro gene of FIV and pAB041 comprising the G gene of the rabies virus.

For vaccination of avian species, the invention may apply in particular to vaccination against the Marek's disease virus (MDV), the Newcastle disease virus (NDV), the Gumboro disease virus (IBDV or Infectious Bursal Disease Virus), the infectious bronchitis virus (IBV), the infectious anemia virus (CAV), the infectious laryngotracheitis virus (ILTV), the encephalomyelitis virus (AEV or avian leukosis virus ALV), the pneumovirosis virus or pneumovirus, and the avian influenza virus. Among the genes encoding the major immunogens which can be used in the present invention, there may be mentioned most particularly the gB and gD genes for the Marek's disease virus, HN and F for the Newcastle disease virus, VP2 for the Gumboro disease virus, S, M and N for the infectious bronchitis virus, C+NS1 for the infectious anemia virus, gB and gD for the infectious laryngotracheitis virus, env and gag/pro for the encephalomyelitis virus, F and G for the pneumovirosis virus and HA, N and NP for avian influenza. Such polynucleotide vaccine formulas are described in patent application WO-A-98 03 659 (FR-A2,751,225) which is incorporated herein by reference. Persons skilled in the art will therefore be able to refer to the plasmids described in this application in order to combine them with the adjuvants in accordance with the invention. Most particularly, persons skilled in the art will be able to combine, with the adjuvants in accordance with the invention, the plasmids described specifically in this application, namely pAB045 comprising the gB gene of MDV, pAB080 comprising the gD gene of MDV, pAB046 comprising the HN gene of NDV, pAB047 comprising the F gene of NDV, pAB048 comprising the VP2 gene of IBDV, pAB049 comprising the S1 gene of IBV, pAB050 comprising the M gene of IBV, pAB051 comprising the N gene of IBV, pAB054 comprising the VP1 gene of CAV, pAB055 comprising the VP2 gene of CAV, pAB076 comprising the gB gene of ILTV, pAB089 comprising the gD gene of ILTV, pAB086 comprising the env gene of AEV, pAB081 comprising the gag/pro gene of AEV, pAB082 comprising the G gene of the pneumovirus, pAB077 comprising the HA gene of avian influenza, strain H2N2, pAB078 comprising the HA gene of avian influenza, strain H7N7, pAB088 comprising the NP gene of avian influenza, strain H1N1, pAB079 comprising the N gene of avian influenza, strain H7N1.

Each naked, in particular plasmid, DNA comprises a promoter capable of bringing about, in the host cells, the expression of the gene inserted under its control. It will be in general a strong eukaryotic promoter and in particular a cytomegalovirus early promoter CMV-IE, of human or murine origin, or alternatively possibly of another origin such as rat, pig or guinea pig. In a more general manner, the promoter may either be of viral origin, or of cellular origin. As viral promoter other than CMV-IE, there may be mentioned the SV40 virus early or late promoter or the Rous sarcoma virus LTR promoter. It may also be a promoter coming from the virus from which the gene is derived, for example the actual promoter of the gene. As cellular promoter, there may be mentioned the promoter of a cytoskeleton gene, such as for example the desmin promoter (Bolmont et al., Journal of Submicroscopic Cytology and Pathology, 1990, 22, 117–122; and Zhenlin et al., Gene, 1989, 78, 243–254), or alternatively the actin promoter. When several genes are present in the same naked, in particular plasmid, DNA they may be present in the same transcription unit or in two different units.

Of course, a vaccine may combine, for each of the valencies described above, several genes within the same naked, in particular plasmid, DNA and/or several naked, in particular plasmid, DNAs each comprising one or more genes of the same virus.

The subject of the invention is also multivalent recombinant vaccines, that is to say containing one or preferably two or more naked, in particular plasmid, DNAs expressing antigens for two or more diseases, in the form of a mixture in an adjuvant solution in accordance with the invention.

In the ready-for-use vaccine, the naked DNA, in particular the vaccinal plasmid, is present in the quantities normally used and described in the literature.

The subject of the invention is also a method of vaccination consisting of administering by the parenteral, preferably intramuscular, intradermal, route or by the mucosal route a DNA vaccine in accordance with the invention at the rate of one or more administrations.

The subject of the invention is also the use of the adjuvant compounds in accordance with the invention for the production of adjuvant-containing DNA vaccines as described here.

The invention will now be described in greater detail with the aid of the embodiments taken by way of nonlimiting examples and referring to the accompanying figures.

BRIEF DESCRIPTION OF THE DRAWINGS

FIG. 1: Sequence of the hemagglutinin (HA) gene of the equine influenza virus strain Newmarket 2/93

FIG. 2: Sequence of the hemagglutinin (HA) gene of the equine influenza virus strain Kentucky 1/94

FIG. 3: Sequence of the neuraminidase (NA) gene of the equine influenza virus strain Newmarket 2/93

FIG. 4: Sequence of the neuraminidase (NA) gene of the equine influenza virus strain Kentucky 1/94

FIG. 5: Sequence of the nucleoprotein (NP) gene of the equine influenza virus strain Newmarket 2/93

FIG. 6: Sequence of the nucleoprotein (NP) gene of the equine influenza virus strain Kentucky 1/94.

SEQUENCE LISTING

SEQ ID No. 1: Oligonucleotide CCL007
SEQ ID No. 2: Oligonucleotide CCL018
SEQ ID No. 3: Sequence of the HA gene, EIV Newmarket 2/93 strain
SEQ ID No. 4: Oligonucleotide CCL020
SEQ ID No. 5: Sequence of the HA gene, EIV Kentucky 1/94 strain
SEQ ID No. 6: Oligonucleotide AB260
SEQ ID No. 7: Oligonucleotide AB262
SEQ ID No. 8: Sequence of the NA gene, EIV Newmarket 2/93 strain
SEQ ID No. 9: Sequence of the NA gene, EIV Kentucky 1/94 strain
SEQ ID No. 10: Oligonucleotide CCL019
SEQ ID No. 11: Oligonucleotide CCL021
SEQ ID No. 12: Sequence of the NP gene, EIV Newmarket 2/93 strain
SEQ ID No. 13: Sequence of the NP gene, EIV Kentucky 1/94 strain

EXAMPLE 1

Adjuvant

The carbomer used in the vaccines in accordance with the present invention is Carbopol® 974P manufactured by the company BF Goodrich (MW about 3 million).

A stock solution containing 1.5% w/v of Carbopol® 974P was first prepared in distilled water containing sodium chloride at 1 g/l.

This stock solution is then used for the manufacture of a solution of Carbopol® in physiological saline at 4 mg/ml. The stock solution is poured into the entire physiological saline (or optionally into most of it) all at once or optionally in several portions with, each time, adjustment of the pH with the aid of NaOH (for example 1N or more concentrated) to a value of about 7.3 to 7.4.

A ready-for-use solution of Carbopol® is thereby obtained.

EXAMPLE 2

Culture of the Viruses

The viruses are cultured on the appropriate cellular system until a cytopathic effect is obtained. The cellular systems to be used for each virus are well known to the persons skilled in the art. Briefly, cells sensitive to the virus used, cultured in Eagle's minimum essential medium ("MEMN" medium) or another appropriate medium, are inoculated with the viral strain studied using a multiplicity of infection of 1. The infected cells are then incubated at 37° C. for the time necessary for the appearance of a complete cytopathic effect (on average 36 hours).

EXAMPLE 3

Extraction of the Viral Genomic DNAs

After culture, the supernatant and the lysed cells are harvested and the entire viral suspension is centrifuged at 1000 g for 10 minutes at +4° C. in order to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 μg/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After one night at −20° C., the DNA is centrifuged at 10,000 g for 15 minutes at +4° C. The DNA pellet is dried and then taken up in a minimum volume of sterile ultrapure water. It can then be digested with restriction enzymes.

EXAMPLE 4

Isolation of the Viral Genomic RNAs

The RNA viruses were purified according to techniques well known to persons skilled in the art. The genomic viral RNA of each virus was then isolated using the "guanidium thiocyanate/phenol-chloroform" extraction technique described by P. Chomczynski and N. Sacchi (Anal. Biochem, 1987. 162. 156–159).

EXAMPLE 5

Molecular Biology Techniques

All the plasmid constructions were carried out using the standard molecular biology techniques described by J. Sambrook et al. (*Molecular Cloning: A Laboratory Manual*. 2nd Edition. Cold Spring Harbor Laboratory, Cold Spring Harbor, N.Y., 1989). All the restriction fragments used for the present invention were isolated using the "Geneclean" kit (BIO101 Inc. La Jolla, Calif.).

EXAMPLE 6

RT-PCR Technique

Specific oligonucleotides (containing at their 5' ends restriction sites to facilitate the cloning of the amplified fragments) were synthesized so that they completely cover the coding regions of the genes which have to be amplified (see specific examples). The reverse transcription reaction (RT) and polymerase chain reaction (PCR) were carried out according to standard techniques (J. Sambrook et al. *Molecular Cloning: A Laboratory Manual*. 2nd Edition. Cold Spring Harbor Laboratory, Cold Spring Harbor, N.Y., 1989). Each RT-PCR reaction was performed with a pair of specific amplimers and taking as template the extracted viral genomic RNA. The amplified complementary DNA was extracted with phenol/chloroform/isoamyl alcohol (25:24:1) before being digested with restriction enzymes.

EXAMPLE 7

Plasmid pVR1012

The plasmid pVR1012 was obtained from Vical Inc. San Diego, Calif., USA. Its construction has been described in J. Hartikka et al. (Human Gene Therapy. 1996. 7. 1205–1217) incorporated herein by reference.

EXAMPLE 8

Construction of the Plasmid pCCL027

(Newmarket 2/93 EIV HA Gene)
An RT-PCR reaction according to the technique described in Example 6 was carried out with the genomic RNA of the equine influenza virus (EIV) (Newmarket 2/93 strain) (Daly et al. J. Gen. Virol. 1996. 77. 661–671), prepared according to the technique described in Example 4, and with the following oligonucleotides:

```
CCL007 (40 mer) (SEQ ID No.1)
5' TTGTCGACTCAATCATGAAGACAACCATTATTTTGATACT 3'

CCL018 (34 mer) (SEQ ID No. 2)
5' TTGGATCCTTACTCAAATGCAAATGTTGCACCTG 3'
``` in order to isolate the gene encoding the HA glycoprotein of the equine influenza virus (Newmarket 2/93 strain) (FIG. 1, SEQ ID No. 3) in the form of a PCR fragment of about 1750 bp. This fragment was purified and then ligated with the vector pCRII (Cat# K2000-01, Invitrogen Corp. Carlsbad, Calif.) in order to give the plasmid pCCL026. The plasmid pCCL026 was then digested with the restriction enzymes SalI and NotI in order to isolate an SalI-NotI fragment of 1751 bp containing the Newmarket 2/93 EIV HA gene. This fragment was then ligated with the plasmid pVR1012 (see Example 7), previously digested with SalI and NotI, in order to give the plasmid pCCL027 (6642 bp).

EXAMPLE 9

Construction of the Plasmid pPB242

(Kentucky 1/94 EIV HA Gene)

An RT-PCR reaction according to the technique described in Example 6 was carried out with the genomic RNA of the equine influenza virus (EIV) (Kentucky 1/94 strain) (Daly et al. J. Gen. Virol. 1996. 77, 661–671), prepared according to the technique described in Example 4, and with the following oligonucleotides:

```
CCL007 (40 mer) (SEQ ID No. 1)
5' TTGTCGACTCAATCATGAAGACAACCATTATTTTGATACT 3'

CCL020 (34 mer) (SEQ ID No. 4)
5' TTGGATCCTTACTCAAATGCAAATGTTGCATCTG 3'
``` in order to isolate the gene encoding the HA glycoprotein of the equine influenza virus (Kentucky 1/94 strain) (FIG. 2, SEQ ID No. 5) in the form of a PCR fragment of about 1750 bp. This fragment was purified and then ligated with the vector pCRII (Cat# K2000-01, Invitrogen Corp. Carlsbad, Calif.) in order to give the plasmid pCCL028. The plasmid pCCL028 was digested with the restriction enzymes SacI and BamHI in order to isolate an SacI-BamHI fragment of 1153 bp (fragment A) containing the 3' part of the Kentucky 1/94 EIV HA gene. The plasmid pCCL028 was digested with the restriction enzymes SacI and EcoRV in order to isolate a SacI-EcoRV fragment of 621 bp (fragment B) containing the 5' part of the Kentucky 1/94 EIV HA gene. Fragments A and B were then ligated together with the plasmid pVR1012 (see Example 7), previously digested with EcoRV and BamHI, in order to give the plasmid pPB242 (6688 bp).

EXAMPLE 10

Construction of the Plasmid pAB142

(Newmarket 2/93 EIV NA Gene)

An RT-PCR reaction according to the technique described in Example 6 was carried out with the genomic RNA of the equine influenza virus (EIV) (Newmarket 2/93 strain) (Daly et al. J. Gen. Virol. 1996, 77, 661–671), prepared according to the technique described in Example 4, with the following oligonucleotides:

```
AB260 (35 mer) (SEQ ID No. 6)
5' TTTGTCGACATGAAYCCAAATCAAAARATAATAAC 3'

AB262 (32 mer) (SEQ ID No. 7)
5' TTTGGATCCYTACATCTTRTCGATGTCAAAGG 3'
``` in order to isolate the gene encoding the neuraminidase (NA) glycoprotein of the equine influenza virus (Newmarket 2/93 strain) (FIG. 3, SEQ ID No. 8) in the form of a PCR fragment of about 1430 bp. This fragment was purified and then digested with the restriction enzymes SalI and BamHI in order to isolate a SalI-BamHI fragment of 1418 bp containing the Newmarket 2/93 EIV NA gene. This fragment was then ligated with the plasmid pVR1012 (see Example 7), previously digested with SalI and BamHI, in order to give the plasmid pAB142 (6287 bp).

EXAMPLE 11

Construction of the Plasmid pPB246

(Kentucky 1/94 EIV NA Gene)

An RT-PCR reaction according to the technique described in Example 6 was carried out with the genomic RNA of the equine influenza virus (EIV) (Kentucky 1/94 strain) (Daly et al. J. Gen. Virol. 1996, 77, 661–671), prepared according to the technique described in Example 4, and with the following oligonucleotides: AB260 and AB262 (Example 10) in order to isolate the gene encoding the neuraminidase (NA) glycoprotein of the equine influenza virus (Kentucky 1/94 strain) (FIG. 4, SEQ ID No. 9) in the form of a PCR fragment of about 1430 bp. This fragment was purified and then digested with the restriction enzymes SalI and BamHI in order to isolate a SalI-BamHI fragment of 1418 bp containing the Kentucky 1/94 EIV NA gene. This fragment was then ligated with the plasmid pVR1012 (see Example 7), previously digested with SalI and BamHI, in order to give the plasmid pAB116 (6287 bp).

EXAMPLE 12

Construction of the Plasmid pPB245

(Newmarket 2/93 EIV NP Gene)

An RT-PCR reaction according to the technique described in Example 6 was carried out with the genomic RNA of the equine influenza virus (EIV) (Newmarket 2/93 strain) (Daly et al. J. Gen. Virol. 1996, 77, 661–671), prepared according to the technique described in Example 4, and with the following oligonucleotides:

```
CCL019 (25 mer) (SEQ ID No. 10)
5' TTGTCGACCATGGCGTCTCAAGGCAC 3'

CCL021 (28 mer) (SEQ ID No. 11)
5' TTTCTAGACTTTAAYTGTCAWACTCYTC 3'
``` in order to isolate the gene encoding the nucleoprotein (NP) of the equine influenza virus (Newmarket 2/93 strain) (FIG. 5, SEQ ID No. 12) in the form of a PCR fragment of about 1520 bp. This fragment was purified and then digested with the restriction enzymes SalI and XbaI in order to isolate a SalI-XbaI fragment of 1506 bp containing the Newmarket 2/93 EIV NP gene. This fragment was then ligated with the plasmid pVR1012 (see Example 7), previously digested with SalI and XbaI, in order to give the plasmid pPB245 (6389 bp).

EXAMPLE 13

Construction of the Plasmid pPB246

(Kentucky 1/94 EIV NP Gene)

An RT-PCR reaction according to the technique described in Example 6 was carried out with the genomic RNA of the equine influenza virus (EIV) (Kentucky 1/94 strain) (Daly et al. J. Gen. Virol. 1996, 77, 661–671), prepared according to the technique described in Example 4, and with the following oligonucleotides: CCL019 and CCL021 (Example 12) in order to isolate the gene encoding the nucleoprotein (NP) of the equine influenza virus (Kentucky 1/94 strain) (FIG. 6, SEQ ID No. 13) in the form of a PCR fragment of about 1520 bp. This fragment was purified and then digested with the restriction enzymes SalI and XbaI in order to isolate a SalI-XbaI fragment of 1506 bp containing the Kentucky 1/94 EIV NP gene. This fragment was then ligated with the plasmid pVR1012 (see Example 7), previously digested with SalI and XbaI, in order to give the plasmid pPB246 (6389 bp).

EXAMPLE 14

Construction of the Plasmid pPB156

(BHV-1 gB Gene)

Its construction is described in WO-A-98 03200.

EXAMPLE 15

Construction of the Plasmid pAB087

(BHV-1 gD Gene)

Its construction is described in WO-A-98 03200.

EXAMPLE 16

Construction of the Plasmid pAB090

(PRV gB Gene)

Its construction is described in WO-A-98 03658.

EXAMPLE 17

Construction of the Plasmid pPB098

(PRV gD Gene)

Its construction is described in WO-A-98 03658.

EXAMPLE 18

Construction of the Plasmid pAB044

(CDV HA Gene)

Its construction is described in WO-A-98 03199.

EXAMPLE 19

Construction of the Plasmid pAB036

(CDV F Gene)

Its construction is described in WO-A-98 03199.

EXAMPLE 20

Construction of the Plasmid pAB041

(G Gene of the Rabies Virus)

Its construction is described in WO-A-98 03199.

EXAMPLE 21

Application in Horses

The vaccine tested is a mixture of 3 plasmids pCCL027 (Example 8), pAB142 (Example 10) and pPB245 (Example 12) containing and expressing, respectively, the HA, NA and NP genes of the EIV virus strain Newmarket 2/93. This mixture is combined or otherwise with the carbomer as according to the present invention.

The vaccination/challenge protocol was the following:

| Group | Number of horses | Vaccine | Diluent | Dose |
|---|---|---|---|---|
| A | 5 | pCCL027 + pAB142 + pPB245 | Saline solution | 3 × 400 µg |
| B | 5 | pCCL027 + pAB142 + pPB245 | Carbopol ® 974P | 3 × 400 µg |
| C | 6 | Commercial vaccine | — | 1 commercial dose |
| D (controls) | 5 | — | — | — |

Ponies (Welsh Mountain ponies) 7 to 8 months old, having no detectable antibodies against the H3N8 and H7N7 viruses, measured by the SRH (Single Radial Haemolysis) test, were used for this study. The ponies were randomly distributed into 4 groups.

The horses were vaccinated on D0 and D35 by the intramuscular route. The commercial vaccine used for group C was administered to the horses in a dose volume of 1 ml.

The ponies in groups A and B each received 2 doses of 5 ml on D0 and D35 by deep intramuscular injection into the neck.

On D56, three weeks after the second vaccination, each pony was infected by exposure to an aerosol obtained from about 1 ml of allantoic fluid containing a total of $10^{7.3}$ $EID_{50}$ of influenza A-equi-2/Sussex/89 virus, using an ULTRA 2000 model spraying device (De Vilbiss, Somerset Pa.), as described by Mumford et al., Equine Vet. J. 1990, 22, 93–98.

After the challenge, the ponies were monitored in order to observe the clinical signs (establishment of a clinical score) and the temperature. Nasal swabs were prepared daily from day 0 of the challenge up to the 10th day after the challenge in order to measure the quantity of virus excreted by each challenged horse.

Finally, blood samples were collected throughout the protocol, before and after the challenge (days D0, D7, D14, D35, D49, D56, D63 and D70) in order to measure the kinetics of appearance and the level of SRH and IHA antibodies (haemagglutinating antibodies) for each vaccinated group.

EXAMPLE 22

Application in Pigs

The efficacy of a plasmid vaccine, combined or otherwise with the carbomer, was studied in pigs in a vaccination/challenge model for Aujeszky's disease. The vaccine tested is a mixture of 2 plasmids pAB090 (Example 16) and pPB098 (Example 17) comprising and expressing, respectively, the gB and gD genes of the PRV virus. The mixture was combined or otherwise with the carbomer as according to the present invention. The vaccination/challenge protocol used was the following:

| Group | Number of pigs | Vaccine | Diluent | Dose |
|---|---|---|---|---|
| A | 6 | pPB098 + pAB090 | Saline solution | 2 × 200 µg |
| B | 6 | pPB098 + pAB090 | Carbopol ® 974P | 2 × 200 µg |
| C | 6 | Geskypur | — | 1 commercial dose |
| D (controls) | 6 | — | — | — |

On D0, the pigs in groups A and B were vaccinated with the mixture of the plasmids pPB098 and pAB090 (200 µg of each plasmid), combined or otherwise with the carbomer, by the intramuscular route, in a volume of 2 ml.

The pigs in group C received an injection of the commercial vaccine Geskypur (subunit vaccine, MERIAL, Lyon, France) by the intramuscular route in a volume of 2 ml.

The pigs in group D were not vaccinated.

On D21, all the pigs were challenged with 2 ml (at the rate of 1 ml per nostril) of a viral suspension of Aujeszky's challenge strain, strain NIA3 (1/5 dilution of a stock solution titrating $10^{8.25}$ $CCID_{50}$/ml).

After the challenge, the pigs were monitored for mortality and the delta G7 criterion (individual weighings on D0 and D7 of the challenge). Nasal swabs are prepared daily from D0 to D14 of the challenge in order to measure the quantity of virus excreted after the challenge.

Finally, blood samples were collected on D0, D7, D14, D21 and D28 of the protocol in order to measure the kinetics and the Aujeszky's disease virus (PRV) seroneutralizing antibody level. The anti-PRV ELISA antibodies of isotypes IgG1 and IgG2 were also measured in the sera collected in the vaccinated and nonvaccinated pigs.

EXAMPLE 23

Application in Bovines

The efficacy of a plasmid vaccine, combined or otherwise with the carbomer, was studied in bovines in a vaccination/challenge model for infectious bovine rhinotracheitis (IBR) or BHV-1. The vaccine tested is a mixture of 2 plasmids pPB156 (Example 14) and pAB087 (Example 15) comprising and expressing, respectively, the gB and gD genes of the BHV-1 virus. The mixture was combined or otherwise with the carbomer as according to the present invention. The vaccination/challenge protocol used was the following:

| Group | Number of calves | Vaccine | Diluent | Dose |
|---|---|---|---|---|
| A | 6 | pAB087 + pPB156 | Saline solution | 2 × 300 µg |
| B | 6 | pAB087 + pPB156 | Carbopol ® 974P | 2 × 300 µg |
| C | 6 | Ibepur | — | 1 commercial dose |
| D (controls) | 6 | — | — | — |

On D0, the calves in groups A and B were vaccinated with the mixture of plasmid pPAB087 and pPB156 (300 µg of each plasmid), combined or otherwise with the carbomer, by the intramuscular route, in a volume of 5 ml.

The calves in group C received an injection of the commercial vaccine Ibepur (subunit vaccine, MERIAL, Lyon, France) by the intramuscular route in a volume of 2 ml.

The calves in group D were not vaccinated.

On D21, groups A, B and C received a second injection of vaccine according to the same modalities as on D0.

On D35, the calves were challenged with 2.5 ml (at the rate of 1.25 ml per nostril) of a viral suspension of the BHV-1 challenge strain, strain B901 (1/5 dilution of a stock solution titrating $10^{8.15}$ $CCID_{50}$/ml).

After the challenge, the calves were monitored for clinical signs (establishment of a clinical score). Nasal swabs were prepared daily from D0 to D14 of the challenge in order to measure the quantity of virus excreted after the challenge. Finally, blood samples were collected on D0, D7, D14, D21, D35 and D49 of the protocol in order to measure the kinetics and the infectious bovine rhinotracheitis virus (BHV-1) seroneutralizing antibody level. The anti-BHV-1 ELISA antibodies of isotypes IgG1 and IgG2 were also measured in these sera collected from vaccinated and nonvaccinated calves.

EXAMPLE 24

Application in Dogs

The efficacy of a plasmid vaccine, combined or otherwise with the carbomer, was studied in dogs in a vaccination/challenge model for Carré's disease (CDV). The vaccine tested is a mixture of the 2 plasmids pAB044 (Example 18) and pAB036 (Example 19) comprising and expressing, respectively, the HA and F genes of the CDV virus. The vaccination/challenge protocol used was the following:

| Group | Number of dogs | Vaccine | Diluent | Dose |
|---|---|---|---|---|
| A | 6 | pAB036 + pAB041 | Saline solution | 2 × 200 µg |
| B | 6 | pAB036 + pAB041 | Carbopol ® 974P | 2 × 200 µg |
| C | 6 | EURICAN | — | 1 commercial dose |
| D (controls) | 6 | — | — | — |

The dogs in groups A, B and C were vaccinated on D0 and D28 by the intramuscular route. The dogs in groups A and B received, for each vaccination, an injection of plasmid solution containing 400 µg in total (2×200 µg) in a volume of 1 ml.

The dogs in group C were vaccinated with the vaccine EURICAN (CHPPI2) which is a vaccine marketed by Mérial, Lyon, France. One commercial dose contains about $10^4$ pfu of CDV Onderstepoort vaccinal strain as well as the valencies for vaccination against Rubarth's hepatitis, canine parvovirosis and type 2 parainfluenza virus.

The challenge was performed on D49 by intracerebral administration of 1/10 dilution of the CDV "Synder-Hill" challenge strain (batch prepared and provided by USDA, USA).

Clinical monitoring was performed daily for 21 days after the challenge in order to note the signs (general state, oculonasal symptoms, digestive symptoms, nervous symptoms, temperature) (notation according to the rules of the European Pharmacopoeia). The challenged dogs were also weighed once per week.

Protection was assessed on the following criteria:
mean clinical scores for each group
CDV viraemia level after challenge (measurement of the viral load in the lymphocytes on D56, D61, D66, D70)
blood count on blood samples collected on D48, D54, D56, D59, D63 and D70 (that is to say days—1, 5, 7, 10, 14 and 21 after challenge)
weight variation after challenge.

For all these criteria, the mean levels for each group were also compared with each other and with the mean level for the control group.

Blood samples were collected on days D0, D14, D28, D56 and D70 for titration of the ELISA antibodies and Carré's disease virus seroneutralizing antibodies.

FURTHER STATEMENT OF THE INVENTION

This invention provides for a DNA vaccine comprising a naked DNA incorporating and expressing in vivo a polynucleotide encoding an antigenic polypeptide, preferably a gene of a pathogenic agent, and at least one adjuvant compound chosen from the polymers of acrylic or methacrylic acid and the copolymers of maleic anhydride and alkenyl derivative.

In one embodiment of the invention, the vaccine is characterized in that it comprises, as adjuvant compound, a polymer of acrylic or methacrylic acid cross-linked with a polyalkenyl ether of a sugar or polyalcohol.

In another embodiment of the invention, the vaccine is characterized in that the polymer is cross-linked with an allyl sucrose or with allylpentaerythritol.

In another embodiment of the invention, the vaccine is characterized in that it comprises, as adjuvant compound, a copolymer of maleic anhydride and ethylene cross-linked, for example, with divinyl ether.

In another embodiment of the invention, the vaccine is characterized in that the adjuvant compound is present in the vaccine in an amount of 0.01% to 2% w/v.

In another embodiment of the invention, the vaccine is characterized in that the concentration is 0.06 to 1% w/v, preferably 0.1 to 0.6% w/v.

In another embodiment of the invention, the vaccine is characterized in that the naked DNA is a plasmid.

In another embodiment of the invention, the adjuvant compound is a carbomer or an EMA®.

In yet another embodiment of the invention, the vaccine is characterized in that it comprises a naked DNA incorporating and expressing a sequence of a pig, horse, dog, bovine, cat or avian pathogen.

In a further embodiment of the invention, the vaccine is characterized in that it comprises at least one sequence of a pathogen chosen from:

Aujeszky's disease virus
porcine influenza virus
porcine reproductive and respiratory syndrome virus
porcine parvovirosis virus
hog cholera virus
*Actinobacillus pleuropneumoniae*
equine rhinopneumonia virus
equine influenza virus
*Cl. Tetani*
Eastern encephalitis virus
Western encephalitis virus
Venezuelan encephalitis virus
*B. burgdorferi*
Canine Distemper virus
canine parvovirus
canine cornoavirus
canine herpesvirus
rabies virus
bovine herpesvirus types 1 or 5
bovine respiratory syncytial virus
bovine pestivirus
bovine parainfluenza virus type 3
feline leukaemia virus
feline panleukopaenia virus
feline infectious paritonitis virus
feline herpesvirus
feline calicivirosis virus
feline immunodeficiency virus
Marek's disease virus
Newcastle disease virus
Gumboro disease virus
avian infectious bronchitis virus
avian infectious anaemia virus
infectious laryngotracheitis virus
avian leukosis virus
avian pneumovirus
avian influenza.

The present invention also provides for a method of enhancing the DNA vaccine incorporating and expressing in vivo a heterologous polynucleotide by adding an adjuvant chosen from the polymers of acrylic or methacrylic acid and the copolymers of maleic anhydride and alkenyl derivative, as defined in the specification.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. A DNA vaccine comprising (i) a naked DNA plasmid containing and expressing in vivo a polynucleotide encoding an antigenic polypeptide, wherein the antigenic polypeptide comprises an antigen of equine rhinopheumonia virus; and (ii) at least one adjuvant which is a polymer of acrylic or methacrylic acid.

2. The vaccine according to claim 1, wherein the adjuvant is present in the vaccine in an amount of 0.01% to 2% w/v.

3. The vaccine according to claim 2 wherein the adjuvant is present in a concentration of 0.06 to 1% w/v.

4. A method of enhancing efficacy of a DNA plasmid vaccine which comprises a naked DNA containing and expressing in vivo a heterologous polynucleotide, wherein the heterologous polynucleotide is an immunogen of equine rhinopheumonia virus, by adding to the DNA plasmid vaccine an adjuvant which is a polymer of acrylic or methacrylic acid.

5. The method of claim 4, wherein the adjuvant has a concentration of 0.06 to 1% w/v.

6. The vaccine of claim 1, wherein the naked DNA plasmid is in the circular plasmid form, wherein the plasmid additionally comprises an origin of replication, a promoter, and a transcription termination sequence.

* * * * *

UNITED STATES PATENT AND TRADEMARK OFFICE
CERTIFICATE OF CORRECTION

| | | |
|---|---|---|
| PATENT NO. | : 7,163,926 B1 | Page 1 of 1 |
| APPLICATION NO. | : 09/677672 | |
| DATED | : January 16, 2007 | |
| INVENTOR(S) | : Jean-Christophe Francis Audonnet | |

It is certified that error appears in the above-identified patent and that said Letters Patent is hereby corrected as shown below:

In The Claims:

Claim 1
Column 29, lines 34 and 35, delete "which is a polymer of acrylic or methacrylic acid" and insert --comprising Carbopol--;

Claim 4
Column 30, lines 31-33, delete "plasmid vaccine an adjuvant which is a polymer of acrylic or methacrylic acid" and insert --vaccine Carbopol--.

Signed and Sealed this

Tenth Day of April, 2007

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 40
<212> TYPE: DNA
<213> ORGANISM: Artificial Sequence
<220> FEATURE:
<223> OTHER INFORMATION: oligonucleotide CCL007

<400> SEQUENCE: 1
ttgtcgactc aatcatgaag acaaccatta ttttgatact                40

<210> SEQ ID NO 2
<211> LENGTH: 34
<212> TYPE: DNA
<213> ORGANISM: Artificial Sequence
<220> FEATURE:
<223> OTHER INFORMATION: Oligonucleotide CCL018

<400> SEQUENCE: 2
ttggatcctt actcaaatgc aaatgttgca cctg                      34

<210> SEQ ID NO 3
<211> LENGTH: 1698
<212> TYPE: DNA
<213> ORGANISM: Artificial Sequence
<220> FEATURE:
<223> OTHER INFORMATION: Sequence of the HA gene, EIV Newmarket 2/93
      strain

<400> SEQUENCE: 3
atgaagacaa ccattatttt gatactactg acccattggg tctacagtca aaacccaacc    60
agtggcaaca acacagccac attatgtctg ggacaccatg cagtagcaaa tggaacattg   120
```

```
gtaaaaacaa taactgatga ccaaattgag gtgacaaatg ctactgaatt agtccagagc        180
atttcaatag ggaaaatatg caacaactca tataggggttc tagatggaag aaattgcaca      240
ttaatagatg caatgctagg agaccccccat tgtgatgatt ttcagtatga gaattgggac      300
ctcttcatag aaagaagcag cgctttcagc aattgctacc catatgacat ccctgactat      360
gcatcgctcc ggtccattgt agcatcctca ggaacattag aattcacagc agagggttc       420 acatggacag tgtcactca aacggaaga agtggagcct gcaaaagggg atcagccgat        480
agtttcttta gccgactgaa ttggctaaca aaatctggaa attcttaccc catattgaat     540
gtgacaatgc ctaacaataa aaatttcgat aaactataca tctgggggat tcatcacccg      600
agctcaaaca aagagcagac aaaattatat atccaagaat caggacgagt aacagtctca     660
acagaaagaa gtcaacaaac agtaatccct aacatcggat ctaggccgtg ggtcagggggt    720 caatcaggca ggataagcat atactggacc attgtaaaac ctggagatat tctaatgata     780
aacagtaatg caacttagt tgcaccgcgg ggatatttta aattgagaac agggaaaagc      840
tctgtaatga gatcagatgc actcatagac acttgtgtgt ctgaatgtat tacaccaaat    900
ggaagcatcc ccaacgacaa accatttcaa aatgtgaaca aaattacata tggaaaatgc    960
cccaagtata tcaggcaaaa cactttaaag ctggccactg ggatgaggaa tgtaccagaa   1020
aagcaaatca gaggaatctt tggagcaata gcgggattca tagaaaacgg ctgggaagga  1080
atggttgatg ggtggtatgg attccgatat caaaactcgg aaggaacagg acaagctgca  1140
gatctaaaga gcactcaagc agccatagac cagatcaatg gaaaattaaa cagagtgatt   1200
gaaaggacca atgagaaatt ccatcaaata gaaaaggaat ctcagaagt agaagggaga   1260 atccaggatt tggagaagta tgtagaagac accaaaatag acctatggtc ctacaatgca   1320
gaattgctgg tggctctaga aaatcaacat acaattgact taacagatgc agaaatgaat   1380
aaattattcg agaagactag cgccagtta agagaaacg cggaagacat gggaggtgga  1440
tgtttcaaga tttaccacaa atgtgataat gcatgcattg gatcaataag aaatgggaca  1500
tatgaccatt acatatacag agatgaagca ttaaacaacc gatttcaaat caaaagtgtt   1560
gagttgaaat caggctacaa agattggata ctgtggattt cattcgccat atcatgcttc   1620
ttaatttgcg ttgttctatt gggtttcatt atgtgggctt gccaaaaagg caacatcagg   1680
tgcaacattt gcatttga                                                  1698

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide CCL020

<400> SEQUENCE: 4
ttggatcctt actcaaatgc aaatgttgca tctg                                 34

<210> SEQ ID NO 5
<211> LENGTH: 1698
<212> TYPE: DNA
<213> ORGANISM: Artificial Sequence
<220> FEATURE:
<223> OTHER INFORMATION: Sequence of the HA gene, EIV Kentucky 1/94
      strain

<400> SEQUENCE: 5
atgaagacaa ccattatttt gatactactg acccattggg tctacagtca aaacccaacc        60
```

```
agtggcaaca acacagccac attatgtctg ggacaccatg cagtagcaaa tggaacattg      120
gtaaaaacaa taactgatga ccaaattgag gtgacaaatg ctactgaatt agttcagagc      180
atttcaatag ggaaaatatg caacaactca tatagagttg tagatggaag aaattgcaca      240
ttaatagatg caatgctagg agaccccac tgtgatgtct ttcagtatga gaattgggac       300
ctcttcatag aaagaagcag cgctttcagc aattgctacc catatgacat ccctgactat      360
gcatcgctcc ggtccattgt agcatcctca ggaacattgg aattcacagc agagggattc      420
acatggacag tgtcactca aaacggaaga agtggagcct gcaaaagggg atcagccgat       480
agtttcttta gccgactgaa ttggctaaca aaatctggaa actcttaccc cacattgaat      540
gtgacaatgc ctaacaataa aaatttcgac aaactataca tctgggggat tcatcacccg      600
agctcaaacc aacagcaaac agaattgtac atccaagaat caggacgagt aacagtctca      660
acaaaaagaa gtcaacaaac gataatccct aatatcggat ctagaccgtg ggtcaggggt      720
caatcaggca ggataagcat atactggacc attgtaaaac ctggagatat cctaatgata      780
aacagtaatg caacttagt tgcaccgcgg ggatatttta aattgaaaac agggaaaagc       840
tctgtaatga gatcagatgc acccatagac atttgtgtgt ctgaattatt acaccaaatg      900
gaagcatccc caacgacaaa ccatttcaaa atgtgaacaa agttacatat ggaaaatgcc      960
ccaagtatat caggcaaaac actttaaagc tggccactgg gatgaggaat gtaccagaaa     1020
agcaaatcag aggaatcttt ggagcaatag cgggattcat agaaacggc tgggaaggaa      1080 tggttgatgg gtggtatgga ttccgatatc aaaactcgga aggaacagga caagctgcag     1140
atctaaaaga gcactcaagc agccatcgac cagattaatg gaaaattaaa cagagtgatt     1200
gaaaggacca atgagaaatt ccatcaaata gagaaggaat tctcagaagt agaagggaga     1260
atccaggact ggagaagta tgtagaagac accaaaatag acctatggtc ctacaatgca     1320
gaattgctgg tggctctaga aaatcaacat acaattgact aacagatgc agaaatgaat     1380 aaattattcg agaagactag acgccagtta agagaaaacg cggaagacat gggaggtgga     1440
tgtttcaaga tttaccacaa atgtgataat gcatgcattg gatcaataag aaatgggaca     1500
tatgaccatt acatatacag agatgaagca ttaaacaacc gatttcaaat caaaggtgtt     1560
gagttgaaat caggctacaa agattggata ctgtggattt cattcgccat atcatgcttc     1620
ttaatttgcg ttgttctatt gggtttcatt atgtgggctt gccaaaaagg caacatcaga     1680
tgcaacattt gcatttga                                                   1698
```

<210> SEQ ID NO 6
<211> LENGTH: 35
<212> TYPE: DNA
<213> ORGANISM: Artificial Sequence
<220> FEATURE:
<223> OTHER INFORMATION: Oligonucleotide AB260

<400> SEQUENCE: 6
tttgtcgaca tgaayccaaa tcaaaarata ataac                                 35

<210> SEQ ID NO 7
<211> LENGTH: 32
<212> TYPE: DNA
<213> ORGANISM: Artificial Sequence
<220> FEATURE:
<223> OTHER INFORMATION: oligonucleotide AB262

<400> SEQUENCE: 7

-continued tttggatccy tacatcttrt cgatgtcaaa gg                32

<210> SEQ ID NO 8
<211> LENGTH: 1412
<212> TYPE: DNA
<213> ORGANISM: Artificial Sequence
<220> FEATURE:
<223> OTHER INFORMATION: Sequence of the NA gene, EIV Newmarket 2/93
      strain

<400> SEQUENCE: 8

| | |
|---|---|
| atgaacccaa atcaaaagat aataacaatt ggatctgcat cattaggagt actaatcctc | 60 |
| aacgtcattc tccatgtagt cagcattata gtaacagtac tggttctcaa taacaatgga | 120 |
| acaggtctga actgcaacgg gacgatcata agagagtaca atgaaacagt aagagtagaa | 180 |
| agaatcaccc aatggtataa tactagtaca attgagtaca tagaaagatc ttcaaatgaa | 240 |
| tactacatga caacaccga accactttgt gaggcccagg gctttgcacc attttccaaa | 300 |
| gacaatggaa tacgaattgg gtcgagaggc catgttttg taataagaga acctttgta | 360 |
| tcatgttcgc cctcagaatg tagaaccttt ttcctcacac agggctcatt actcaatgac | 420 |
| aaacattcta acggcacagt gaaggaccga agtccatata ggactttgat gagtgtcaaa | 480 |
| ataggcaat cacctaatgt gtatcaagct aggtttgaat cggtggcatg gtcagcaaca | 540 |
| gcatgccatg atggaaaaaa tggatgacag ttggagtcac agggccccgac aatcaagcag | 600 |
| ttgcagtagt gaactatgga ggtgttccgg ttgatattat taattcatgg gcatgggata | 660 |
| tcttaagaac ccaagaatcg tcatgcacct gcattaaagg agactgttat tgggtgatga | 720 |
| ctgatggacc ggcaaacagg caagctaaat ataggatatt caaagcaaaa aatggaagaa | 780 |
| taattgggca gactgatata agtttcaatg ggggacacat agaggagtgt tcttgttacc | 840 |
| ccaatgaagg gaaggtggaa tgcatatgca gggacaactg gactggaaca aatagaccaa | 900 |
| ttctggtaat atcttctgat ctatcgtaca cagtcggata tttgtgtgct ggcattccca | 960 |
| ctgacactcc tagggagag gatagtcaat tcacaggctc atgtacaagc cctttgggaa | 1020 |
| ataaaggata cggtgtaaaa ggtttcgggt ttcgacaagg aactgacgta tgggccggaa | 1080 |
| ggacaattag taggacttca agatcaggat tcgaaataat aaagatcagg aatggttgga | 1140 |
| cacagaatag taaagatcaa atcagaaggc aagtgattat tgataaccta aattggtcag | 1200 |
| gatatagcgg ttcttccaca ttgccggttg aactaacaaa aaagggatgt ttagtcccct | 1260 |
| gtttctgggt tgaaatgatt agaggtaaac ctgaagaaac aacaatatgg acctctagca | 1320 |
| gctccattgt gatgtgtgga gtagatcata agttgccag ttggtcatgg cacgatggag | 1380 |
| ctattcttcc ctttgacatc gataagatgt aa | 1412 |

<210> SEQ ID NO 9
<211> LENGTH: 1414
<212> TYPE: DNA
<213> ORGANISM: Artificial Sequence
<220> FEATURE:
<223> OTHER INFORMATION: Sequence of the NA gene, EIV Kentucky 1/94
      strain

<400> SEQUENCE: 9

| | |
|---|---|
| atgaatccaa atcaaaagat aataacaatt ggatctgcat cattgggaat attaatcatc | 60 |
| aacgtcattc tccatgtagt cagcattata gtaacagtac tggtcctcaa taacaatgga | 120 |
| acaggtctga actgcaaagg gacgatcata agagagtaca atgaaacaat aagagtagaa | 180 |
| agaattactc aatggtataa taccagtaca attgagtaca tagagagacc ttcaaatgaa | 240 |

-continued

```
tactacatga acaacaccga accactttgt gaggcccaag gctttgcacc attttccaaa    300
gataatggaa tacgaattgg gtcgagaggc catgtttttg taataagaga accttttgtc    360
tcatgttcgc cctcagaatg tagaacettt ttcctcacac agggctcatt actcaatgac    420
aaacattcta acggcacagt gaaggaccga agtccatata ggactttgat gagtgtcaaa    480
ataggcaat cacctaatgt gtatcaagct aggtttgaat cggtggcatg gtcagcaaca     540
gcatgccatg atggaaaaaa atgatgaca gttggagtca cagggcccga taatcaagca     600
attgcagtag tgaactatgg aggtgttccg gttgatatta ttaattcatg gcagggggat    660
atcttaagaa cccaagaatc gtcatgcacc tgcattaaag gagactgtta ttgggtgatg    720
actgatggac cggcaaatag gcaagctaaa tataggatat tcaaagcaaa agatggaaga    780
ataattgggc agactgatat aagtttcaat gggggacaca tagaggagtg ttcttgttac    840
cccaatgaag ggaaggtgga atgcatatgc agggacaact ggactggaac aaatagacca    900
attctggtaa tatcttctga tctatcgtac acagtcggat atttgtgtgc tggcattccc    960
actgacactc ctaggggaga ggatagtcaa ttcacaggct catgtacaag tcctttggga   1020
aataaaggat acggtgtaaa aggtttcggg tttcgacaag gaactgacgt atgggccgga   1080
aggacaatta gtaggacttc aagatcagga ttcgaaataa taaaaatcag gaatggttgg   1140
acacagaaca gtaaagacca aatcagaagg caagtgatta ttgataaccc aaattggtca   1200
ggatatagcg gttcttttcac attgccggtt gaactaacaa aaagggata gtttagtccc   1260
ctgtttctgg gttgaaatga ttagaggtaa acctgaagaa acaacaatat ggacctctag   1320
cagctccatt gtgatgtgtg gagtagatca taaaattgcc agttggtcat ggcacgatgg   1380
agctattctt ccctttgaca tagacaagat gtag                                1414
```

<210> SEQ ID NO 10
<211> LENGTH: 26
<212> TYPE: DNA
<213> ORGANISM: Artificial Sequence
<220> FEATURE:
<223> OTHER INFORMATION: Oligonucleotide CCL019

<400> SEQUENCE: 10

```
ttgtcgacca tggcgtctca aggcac                                           26
```

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide CCL021

<400> SEQUENCE: 11

```
tttctagact ttaaytgtca wactcytc                                         28
```

<210> SEQ ID NO 12
<211> LENGTH: 1497
<212> TYPE: DNA
<213> ORGANISM: Artificial Sequence
<220> FEATURE:
<223> OTHER INFORMATION: Sequence of the NP gene, EIV Newmarket 2/93
      strain

<400> SEQUENCE: 12

```
atggcgtctc aaggcaccaa acgatcttat gagcagatgg aaactgatgg ggaacgccag     60
aatgcaactg aaatcagagc atctgtcgga aggatggtgg gaggaatcgg ccggttttat    120
```

-continued gttcagatgt gtactgagct taaattaaac gaccatgaag ggcggctgat tcagaacagc 180
ataacaatag aaaggatggt actttcggca ttcgacgaaa gaagaaacaa gtacctcgag 240
gagcatccca gtgctgggaa agaccctaag aaaacgggag gcccgatata cagaaggaaa 300
gatgggaaat ggataagaga actcatcctc catgataaag aggaaatcat gagggtctgg 360
cgtcaggcca acaatggtga agatgctact gctggtctta cccatatgat gatctggcac 420
tccaatctca atgacaccac ataccaaaga acaagggctc ttgttcggac tgggatggat 480
cccagaatgt gctctctgat gcaaggatca accctcccac ggagatctgg agctgccggt 540
gctgcagtaa aaggtgttgg aacaatgata atggaactca tcaggatgat caaacgcggg 600
ataaatgatc gaaatttctg gagaggtgaa aatggtcgaa gaaccagaat tgcttatgaa 660
agaatgtgca atatcctcaa agggaaattt caaacagcag cacaacgggc tatgatggaa 720
ccaagtgagg gagggccgca atcctggaaa tgctgagatt gaggatctca ttttcttggc 780
acgatcagca ctcatttgag aggatcagta gcccataaat catgcctacc tgcctgtgtt 840
tatggccttg cagtaaccag tgggtatgac tttgagaagg aaggatactc tctggttggg 900
attgatcctt tcaaactact ccagaacagc caaattttca gtctaatcag accgaaagaa 960
aatccagcac acaagagcca gttggtgtgg atggcatgcc attctgcagc atttgaggac 1020
ctgagagttt tgaatttcat tagaggaaca aaagtaatcc caagaggaca gttggcaacc 1080
agaggagtgc agattgcttc aaatgaaaac atggagaaca atagattcta gcacactcga 1140
actgagaagc agatattggg caataaggac cagaagtgga ggaaacacca gtcaacagag 1200
agcatctgca ggacagataa gtgtgcaacc tactttctca gtgcagagaa atcttccctt 1260
tgaaagagca accattatgg ctgcatttac tgggaacact gagcggagga cttccgacat 1320
gagaacggaa atcataagga tgatggaaaa tgccaaatca gaagatgtgt ctttccaggg 1380
gcggggagtc ttcgagctct cggacgaaaa ggcaacgaac ccgatcgtgc cttcctttga 1440
catgacaatg aagggtctta tttcttcgga gacaatgctg aggagtatga cagttaa 1497

<210> SEQ ID NO 13
<211> LENGTH: 1494
<212> TYPE: DNA
<213> ORGANISM: Artificial Sequence
<220> FEATURE:
<223> OTHER INFORMATION: Sequence of the NP gene, EIV Kentucky 1/94 strain

<400> SEQUENCE: 13
catggcgtct caaggcacca aacgatctta tgagcagatg gaaactgatg gggaacgcca 60
gaatgcaact gaaatcagag catctgtcgg aaggatggtg ggaggaatcg gccggtttta 120
tgttccagat gtgtactgag cttaaactaa acgaccatga agggcggctg attcagaaca 180
gcataacaat agaaaggatg gtactctcgg cattcgacga aagaagaaac aagtatctcg 240
aggagcatcc cagtgctggg aaagacccta agaaaacggg aggcccgata tacagaagga 300
aagatgggaa atggatgaga gaactcatcc tccatgataa agaagaaatc atgaggatct 360
ggcgtcaggc caacaatggt gaagacgcta ctgctggtct tactcatatg atgatctggc 420
actccaatct caatgacacc aaagaacaag ggctcttgtt cggactggga tggatcccag 480
aatgtgctct ctgatgcaag gctcaaccct cccacggaga tctggagccg ctggtgctgc 540
agtaaaaggt gttggaacaa tggtaatgga actcatcaga atgatcaaac gcgggataaa 600
tgatcggaat ttctggagag gtgaaaatag gtcgaagaac cagaattgct tatgaaagaa 660

```
tgtgcaatat cctcaaaggg aaatttcaga cagcagcaca acgggctatg atggaccagg    720
tgagggaagg ccgcaatcct ggaaacgctg agattgagga tctcattttc ttggcacgat    780
cagcacttat tttgagagga tcagtagccc ataaatcatg cctacctgcc tgtgtttatg    840
gccttgcagt aaccagtggg tatgactttg agaaggaagg atactctctg gttggaattg    900
atcctttcaa actactccag aacagccaaa ttttcagtct aatcagaccg aaagaaaacc    960
cagcacacaa gagccagttg gtgtggatgg catgccattc tgcagcattt gaggacctga    1020
gagttttgaa tttcattaga ggaaccaaag taatcccaag aggacagtta gcaaccagag    1080
gagtgcaaat tgcttcaaat gaaaacatgg agacaataga ttctagcaca ctcgaactga    1140
gaagcaaata ttgggcaata aggaccagaa gtggaggaaa acaccagtca acagagagca    1200
tctgcaggac agataagtgt gcaacctact ttctcagtgc agagaaatct tcccttgaa    1260 agagcaacca ttatggctgc attcactggg aacactgaag ggaggacttc cgacatgaga    1320
acggaaatca taaggatgat ggaaaatgcc aaatcagaag atgtgtcttt ccagggggcgg    1380 ggagtcttcg agctctcgga cgaaaaggca acgaacccga tcgtgccttc ctttgacatg    1440
agcaatgaag ggtcttattt cttcggagac aatgctgagg agtttgacaa ttaa    1494
```